(12) United States Patent
Booth, III et al.

(10) Patent No.: US 8,840,592 B2
(45) Date of Patent: Sep. 23, 2014

(54) PISTON FOR MATERIAL DELIVERY SYSTEM

(75) Inventors: William M. Booth, III, Paw Paw, WI (US); Aashiish Agnihotri, Memphis, TN (US); Jeffrey M. Gross, Vancover (CA); Michael Johnson, West Olive, MI (US); Joseph J. Saladino, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1273 days.

(21) Appl. No.: 12/046,856

(22) Filed: Mar. 12, 2008

(65) Prior Publication Data

US 2009/0234363 A1    Sep. 17, 2009

(51) Int. Cl.
*A61M 5/00* (2006.01)
*A61B 17/88* (2006.01)
*A61M 5/315* (2006.01)
*A61M 5/31* (2006.01)

(52) U.S. Cl.
CPC .. *A61B 17/8822* (2013.01); *A61M 2005/31598* (2013.01); *A61B 17/8827* (2013.01); *A61M 2005/3123* (2013.01); *A61M 2005/3128* (2013.01)
USPC .......................................... 604/236; 604/218

(58) Field of Classification Search
USPC ............... 604/218–231, 236; 222/129, 541.3; 606/92–94
See application file for complete search history.

(56) References Cited

U.S. PATENT DOCUMENTS

| | | | |
|---|---|---|---|
| 4,776,704 A * | 10/1988 | Kopunek et al. | 366/184 |
| 5,114,240 A * | 5/1992 | Kindt-Larsen et al. | 366/129 |
| 5,588,745 A | 12/1996 | Tanaka et al. | |
| 5,797,679 A | 8/1998 | Grulke et al. | |
| 5,857,771 A | 1/1999 | Draenert | |
| 6,176,607 B1 | 1/2001 | Hajianpour | |
| 6,536,937 B1 | 3/2003 | Burchett | |
| 6,755,563 B2 | 6/2004 | Wahlig et al. | |
| 7,134,782 B2 | 11/2006 | Coffeen et al. | |
| 2007/0161970 A1 * | 7/2007 | Spohn et al. | 604/533 |

* cited by examiner

*Primary Examiner* — Kami A Bosworth
*Assistant Examiner* — Imani Hayman
(74) *Attorney, Agent, or Firm* — Sorell Lenna & Schmidt LLP

(57) ABSTRACT

A piston configured to be received within a syringe is disclosed. The piston includes a valve body defining a proximal end and a distal end, a filter disposed within the proximal end of the valve body, and a valve disk disposed within the distal end of the valve body. As the piston is advanced through the syringe, the valve disk is configured to provide fluid flow through the valve body.

24 Claims, 3 Drawing Sheets

PISTON FOR MATERIAL DELIVERY SYSTEM

FIELD OF THE DISCLOSURE

The present disclosure relates generally to a material delivery system. More specifically, the present disclosure relates to a piston device for material delivery systems.

BACKGROUND

In medical procedures, such as orthopedic procedures, bone cement is commonly used to affix a prosthesis to a bone or joint structure. Bone cement is typically a two-part mixture of a polymer powder and a liquid monomer. Generally, the polymer powder is polymethyl methacrylate (PMMA) and the liquid monomer is methyl methacrylate monomer (MMA). The polymer powder and liquid monomer are mixed just prior to use to enable the proper consistency for application.

Unfortunately, preparation of bone cement can be harmful. The vapors from the methyl metacrylate monomer are noxious and toxic. Exposure to the vapors, even in small doses, can cause lung, liver, and heart valve damage. Consequently, any exposure to the vapors is discouraged and avoided. Accordingly, there is a need for a device that allows an individual to prepare bone cement without any exposure to dangerous and harmful vapors.

DETAILED DESCRIPTION OF THE DRAWINGS

A piston configured to be received within a syringe is disclosed. The piston includes a valve body defining a proximal end and a distal end, a filter disposed within the proximal end of the valve body, and a valve disk disposed within the distal end of the valve body. As the piston is advanced through the syringe, the valve disk is configured to provide fluid flow through the valve body.

In another embodiment, a syringe is disclosed. The syringe includes a chamber defined by an inner wall. The syringe further includes a piston configured to engage the inner wall of the chamber. The piston includes a valve body defining a proximal end and a distal end, a filter disposed within the proximal end of the valve body, and a valve disk disposed within the distal end of the valve body. As the piston is advanced through the chamber, the valve disk is configured to provide fluid flow through the valve body.

In yet another embodiment, a kit is disclosed. The kit includes a syringe, a piston, and a bone cement mixture. The syringe has a chamber defined by an inner wall and the piston is configured to engage the inner wall of the chamber. The piston includes a valve body defining a proximal end and a distal end, a filter disposed within the proximal end of the valve body, and a valve disk disposed within the distal end of the valve body. As the piston is advanced through the chamber, the valve disk is configured to provide fluid flow through the valve body.

In yet another embodiment, a method of treating a patient is disclosed and includes providing a mixture in a syringe. The method includes advancing a piston through the syringe, wherein the piston includes a valve body defined by a distal end and a proximal end, the distal end including a valve disk in an open position, and the proximal end including a filter contained therein. Further, the method includes expressing fluid flow through the valve body when the valve disk is in the open position.

Description of a First Embodiment of a Material Delivery System

Figure 1:
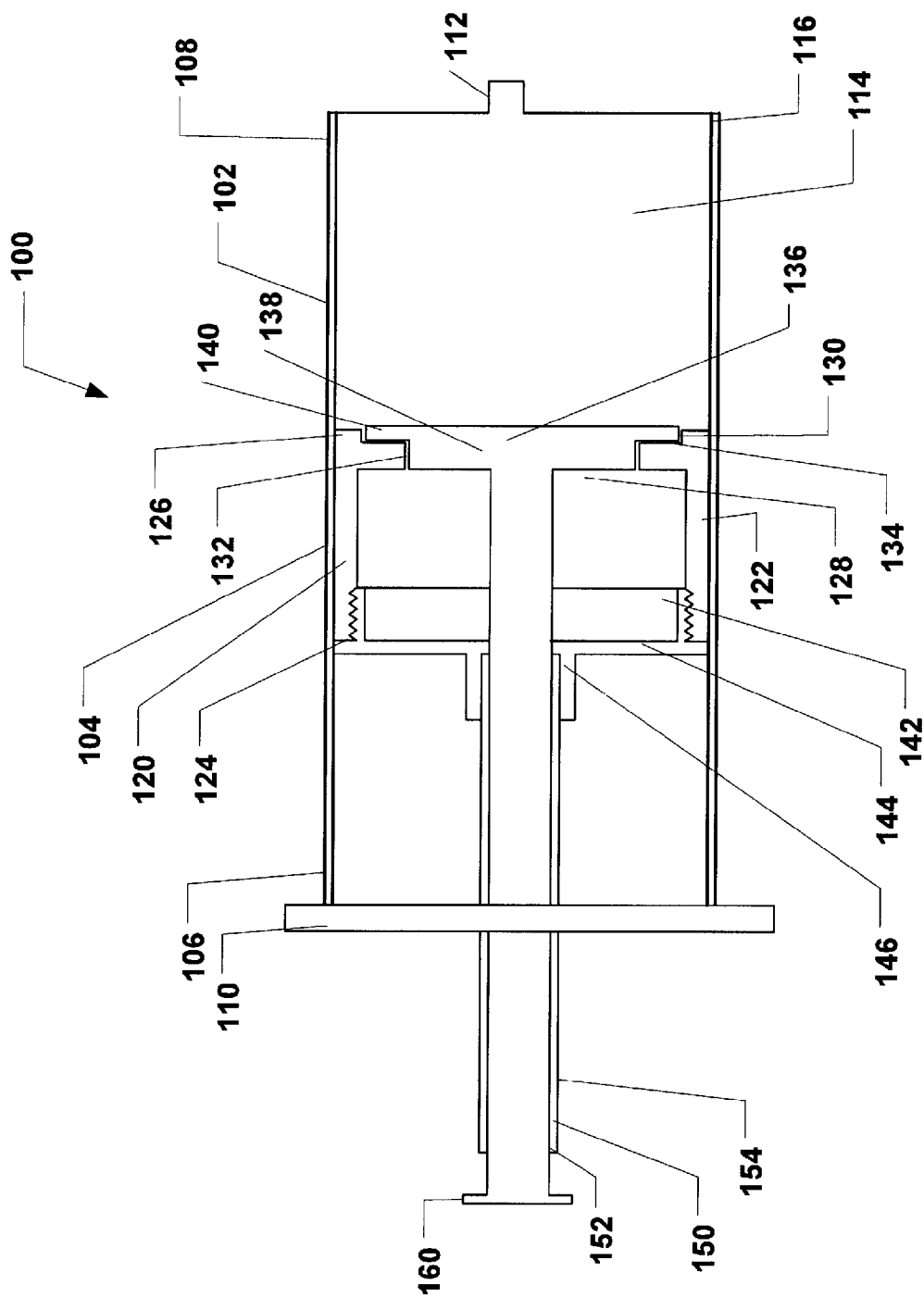
FIG. 1 is a side view of a first embodiment of a material delivery system.

Referring initially to FIG. 1, a first embodiment of a material delivery system is disclosed and is generally designated 100. The material delivery system includes a syringe 102. The syringe 102 can include a barrel 104 that can define a proximal end 106 and a distal end 108. The proximal end 106 of the syringe 102 can include a barrel handle 110. Further, the distal end 108 of the syringe 102 can include a needle hilt 112. Within the barrel 104 of the syringe 102 is a chamber 114 defined by an inner wall 116.

In an embodiment, the chamber 114 of the syringe 102 can be filled with materials (not shown) such as bone cement. Bone cement is typically a two-part mixture of a powdered copolymer and a liquid monomer. The powdered copolymer is typically polymethyl methacrylate (PMMA) and the liquid monomer is typically methyl methacrylate monomer (MMA). The chamber 114 of the syringe 102 can include the two-part mixture and is configured such that the mixture is advanced out of the chamber 114 through the needle hilt 112 when the user is ready to use the mixture. Any configuration of the chamber 114 is envisioned that is suitable for containing material. Typically, the user applies the mixture to the bone of a patient. Alternatively, the user can transfer the mixture to any suitable, separate container.

As shown in FIG. 1, a piston 120 can be disposed within the barrel 104 of the syringe 102. The piston 120 is dimensioned to engage the inner wall 116 of the syringe 102. Typically, the piston 120 may be of any configuration to engage the inner wall 116 of the syringe 102 in a substantially airtight fit. For instance, the piston 120 may be cylindrical in shape and have an outside diameter. Further, the inner wall 116 of the syringe 102 may be cylindrical in shape wherein the outside diameter of the piston 120 is more than the diameter of the inner wall 116 to form a substantially airtight fit. "Substantially airtight fit" as used herein refers to a frictional fit of the inner wall 116 and the piston 120 to prevent any materials from leaving the chamber 114 through the proximal end 106 of the syringe 102.

As seen in FIG. 1, the piston 120 can include a valve body 122 that defines a proximal end 124 and a distal end 126. The distal end 126 of the valve body 122 can include a central bore 128 having a first portion 130 and a second portion 132. At the interface of the first portion 130 and the second portion 132 is a valve seat 134. Included within the central bore 128 of the valve body 122 is a valve plug 136. The valve plug 136 is configured with a central hub 138 and a valve disk 140 that extends from the central hub 138. The valve disk 140 may be incorporated into, or integrally formed with, the central hub 138. Valve disk 138 is configured to engage the valve seat 134 in a concentric fashion. Further, the valve disk 138 is of any suitable configuration to retain any solid or liquid material within the chamber 114 and prevent any solid or liquid material from entering the valve body 122.

Within the proximal end 124 of the valve body 122 is a filter 142. The filter 142 can be of any suitable shape to fit within the valve body 122. In an embodiment, the filter 142 is generally cylindrical and has a filter base 144 and a central filter hub 146. In an exemplary embodiment, the filter 142 is configured to filter gas. As stated earlier, the vapors from the methyl methacrylate monomer are toxic. Typically, the filter 142 is configured to filter noxious gas such as the methyl methacrylate monomer vapors contained within the chamber 114. In an embodiment, the filter 142 may contain any device that can filter gas. In an embodiment, the filter 142 is a charcoal filter. The filter 142 traps the noxious vapors so they are contained within the piston 120. Hence, the vapors are not released into the ambient environment.

The proximal end 124 of the valve body 122 can include a stem 150. The stem 150 is configured to move the piston 120 within the syringe 102. In an exemplary embodiment, as the piston 120 is depressed, the piston 120 moves toward the distal end 108 of the syringe 102. The stem 150 as illustrated is a bar having a round cross-section. Alternatively, the stem 150 can have any cross-section that can be engaged for movement such as square, rectangular, any polygonal shape, or a combination thereof. As shown in FIG. 1, stem 150 includes an inner shaft 152 and an outer shaft 154. Outer shaft 154 engages with the filter hub 146 of the filter 142. Outer shaft 154 may be incorporated into, or integrally formed with the filter hub 146 of the filter 142. Inner shaft 152 engages with the valve plug 136. Inner shaft 152 may be incorporated into, or integrally formed with the valve plug 136. Further, the inner shaft 152 may be coupled to a piston handle 160.

In a particular embodiment, the piston handle 160 of stem 150 is depressed and the piston 120 advances into the barrel 104 of the syringe 102. In particular, depressing the piston handle 160 moves the inner shaft 152 in relation to the outer shaft 154. Depressing the stem 150 pushes the inner shaft 152 and the valve plug 136 axially toward the distal end 108 of the syringe 102, opening valve disk 140 to a first position. In the first position, the valve disk 140 is disengaged with the valve seat 134. Further, in the first position, the valve disk 140 is open to allow fluid flow between the valve disk 140 and the first portion 130 and second portion 132 of the central bore 128. Hence, the fluid flow is open through the valve disk 140 to the valve body 122. In an exemplary embodiment, the fluid flow through the valve disk 140 is the flow of gaseous vapors. Further, as the piston 120 is advanced, the movement of the piston 120 expresses the fluid flow, i.e. the gaseous vapors, through the valve body 122 and through the filter 142. As the gaseous vapors are expressed through the filter 142, the filter 142 filters and traps the vapors so they are contained within the piston 120.

As the piston 120 is advanced through the chamber 114 of the syringe 102, it engages the mass of the mixture. Once the mass of the mixture is engaged, the valve plug 136 is configured such that the resistance of the mixture closes the valve plug 136 to a second position. In the second position, the valve disk 140 engages and is seated within the valve seat 134 and the valve disk 140 is closed to fluid flow, i.e., the flow of gaseous vapors between the valve disk 140 and the first portion 130 and second portion 132 of the central bore 128. Typically, any gaseous vapors are expelled from the chamber 114 of the syringe 102 and filtered in the filter 142 to prevent any gaseous vapors from being expelled through the needle hilt 112.

Further, the piston 120 can be advanced within the syringe 102 to advance the mixture through the needle hilt 112 and out of the syringe 102. The mixture can be safely deposited directly within a patient or transferred to another container without exposing the patient or the preparer to harmful vapors. In an embodiment, the mixture is deposited on a bone contained within the patient. The mixture can be deposited on any bone where bone cement would be useful at the operative site.

Description of a Second Embodiment of a Material Delivery System

Figure 2:
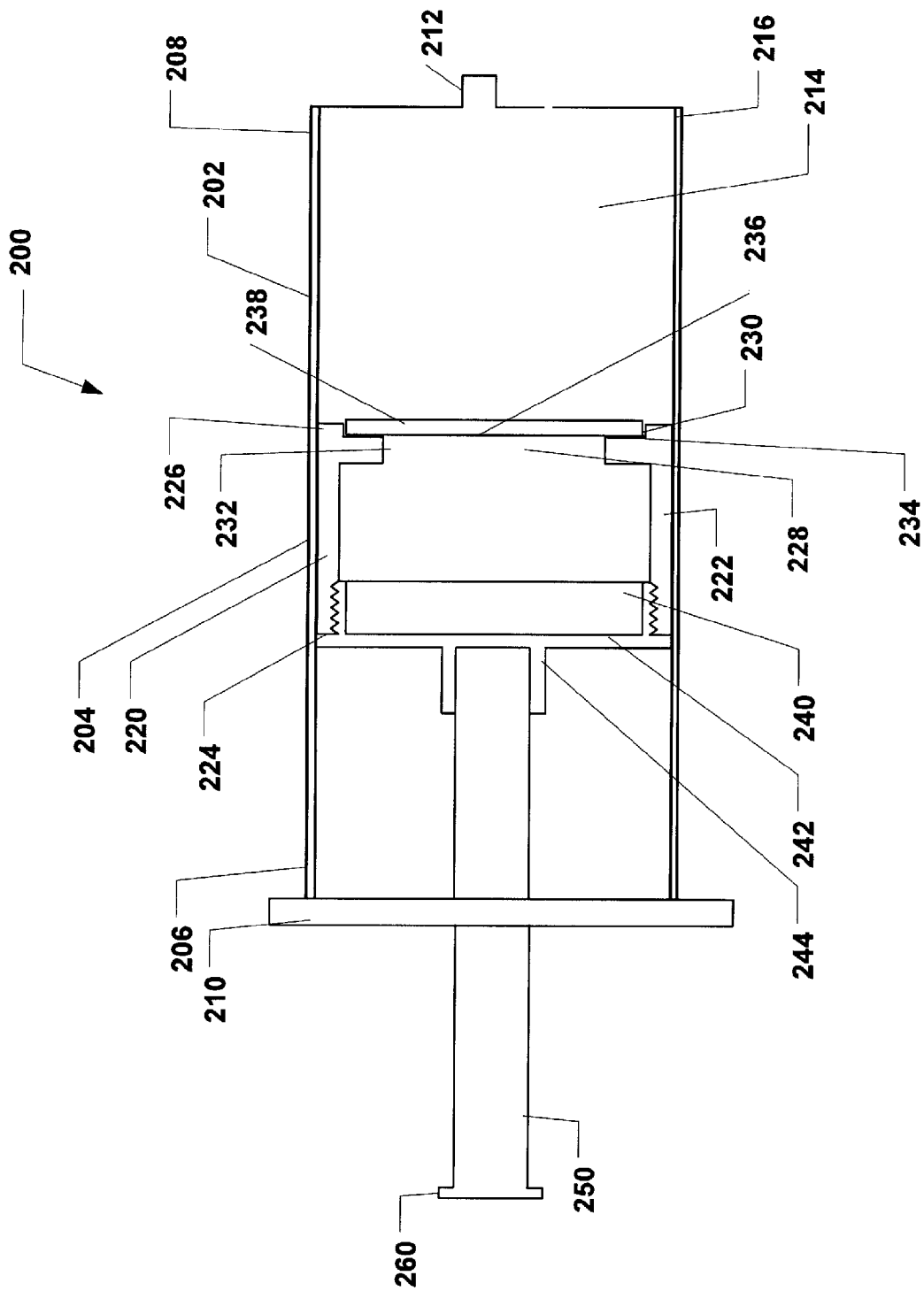
FIG. 2 is a side view of a second embodiment of the material delivery system.

Referring to FIG. 2, a second embodiment of a material delivery system is shown and is generally designated 200. The material delivery system includes a syringe 202. The syringe 202 can include a barrel 204 that can define a proximal end 206 and a distal end 208. The proximal end 206 of the syringe 202 can include a barrel handle 210. Further, the distal end 208 of the syringe 202 can include a needle hilt 212. Within the barrel 204 of the syringe 202 is a chamber 214 defined by an inner wall 216.

In an embodiment, the chamber 214 of the syringe 202 can be filled with materials (not shown) such as bone cement. As described earlier, bone cement is typically a two-part mixture of a powdered copolymer and a liquid monomer. The powdered copolymer is typically polymethyl methacrylate (PMMA) and the liquid monomer is methyl methacrylate monomer (MMA). The chamber 214 of the syringe 202 can include the two-part mixture and is configured such that the mixture is advanced out of the chamber 214 through the needle hilt 212 when the user is ready to use the mixture. Any configuration of the chamber 214 is envisioned that is suitable for containing material. Typically, the user applies the mixture to the bone of a patient. Alternatively, the user can transfer the mixture to any suitable, separate container.

As shown in FIG. 2, a piston 220 can be disposed within the barrel 204 of syringe 202. The piston 220 is configured to engage the inner wall 216 of the syringe 202. Typically, the piston 220 may be of any configuration to engage the inner wall 216 of the syringe 202 in a substantially airtight fit. For instance, the piston 220 may be cylindrical in shape and have an outside diameter. Further, the inner wall 216 of the syringe 202 may be cylindrical in shape wherein the outside diameter of the piston 220 is more than the diameter of the inner wall 216 to form a substantially airtight fit. "Substantially airtight fit" as used herein refers to a frictional fit of the inner wall 216 and the piston 220 to prevent any materials from leaving the chamber 214 through the proximal end 206 of the syringe 202.

The piston 220 can include a valve body 222 that defines a proximal end 224 and a distal end 226. The distal end 226 of the valve body 222 can include a central bore 228 having a first portion 230 and a second portion 232. At the interface of the first portion 230 and the second portion 232 is a valve seat 234. Included within the first portion 230 of the central bore 228 is a valve disk 236. Valve disk 236 is configured to engage the valve seat 234 in a concentric fashion. Further, the valve disk 236 is of any suitable configuration to retain any solid or liquid material within the chamber 214 and prevent any solid or liquid material from entering the valve body 222.

In an embodiment, the valve disk 236 is a porous disk 238. The porous disk 238 may be of any suitable configuration to allow fluid flow through the valve disk 236 to the proximal end 224 of the valve body 222. As illustrated in FIG. 2, the porous disk 238 is configured to engage the valve seat 234 in a concentric fashion. The porous disk 238 may be attached to the valve seat 234 through any suitable technique to physically or chemically attach the porous disk 238. In an exemplary embodiment, the porous disk 238 is permanently affixed to the valve seat 234. The porosity of the porous disk 238 is selected so the porous disk 238 is permeable to fluid flow such as gaseous vapors and is impermeable to liquids or solid particles. Hence, any gaseous vapors within the chamber 214 of the syringe 202, i.e. methyl methacrylate monomer vapors from the bone cement mixture, are circulated through the porous disk 238 to the valve body 222. As the piston 220 is advanced through the syringe 202, the porous disk 238 prevents the mixture from entering valve body 222.

Within the proximal end 224 of the valve body 222 is a filter 240. The filter 240 can be of any suitable shape to fit within the valve body 222. In an embodiment, the filter 240 is generally cylindrical and has a base 242 and a hub 244. The filter 240 is configured to filter gas. As stated earlier, the vapors from the methyl metacrylate monomer are toxic. Typically, the filter 240 is configured to filter noxious gas such as the methyl methacrylate monomer vapors contained within the chamber 214. In an embodiment, the filter 240 may contain any device that can filter gas. In an embodiment, the filter 240 is a charcoal filter. The filter 240 traps the noxious vapors so they are contained within the piston 220. Hence, the vapors are not released into the ambient environment.

The proximal end 224 of the valve body 222 can include a stem 250. The stem 250 is configured to move the piston 220 through the syringe 202. The stem 250 as illustrated is a bar having a round cross-section. Alternatively, the stem 250 can have any cross-section that can be engaged for movement such as square, rectangular, any polygonal shape, or a combination thereof. Stem 250 engages with the filter hub 244 of the filter 240. Stem 250 may be incorporated into, or integrally formed with the filter hub 244 of the filter 240. Further, stem 250 may be coupled to a piston handle 260.

In a particular embodiment, the piston handle 260 of stem 250 is depressed and the piston 220 advances into the barrel 204 of the syringe 202. Depressing the stem 250 pushes the valve disk 236 axially toward the distal end 208 of the syringe 202. The valve disk 236 is in a first position which allows fluid flow through the porous disk 240 to the valve body 222. In an exemplary embodiment, the fluid flow through the valve disk 236 is the flow of gaseous vapors. Further, as the piston 220 is advanced, the movement of the piston 220 expresses the fluid flow through the valve body 222 and through the filter 240. As stated earlier, the filter 240 filters and traps the vapors so they are contained within the piston 220.

As the piston 220 is advanced within the syringe 202, it engages the mass of the mixture. Once the mass of the mixture is engaged, the valve disk 236 is in a closed position wherein the valve disk 236 is closed to fluid flow, i.e., the flow of gaseous vapors. For instance, as the porous disk 238 engages the mixture, the mixture is compressed within the chamber 214 of the syringe 202. The liquid and solid particles of the mixture substantially cover the porous disk 238 so gaseous vapors cannot flow through the porous disk 238. Typically, any gaseous vapors are expelled from the chamber 214 of the syringe 202 and filtered in the filter 240 to prevent any gaseous vapors from being expelled through the needle hilt 212.

Further, the piston 220 can be advanced within the syringe 202 to advance the mixture through the needle hilt 212 and out of the syringe 202. The mixture can be safely deposited directly within a patient or transferred to another container without exposing the patient or the preparer to harmful vapors. In an embodiment, the mixture is deposited on a bone contained within the patient. The mixture can be deposited on any bone where bone cement would be useful at the operative site.

Description of a Method of Treating a Patient

Figure 3:
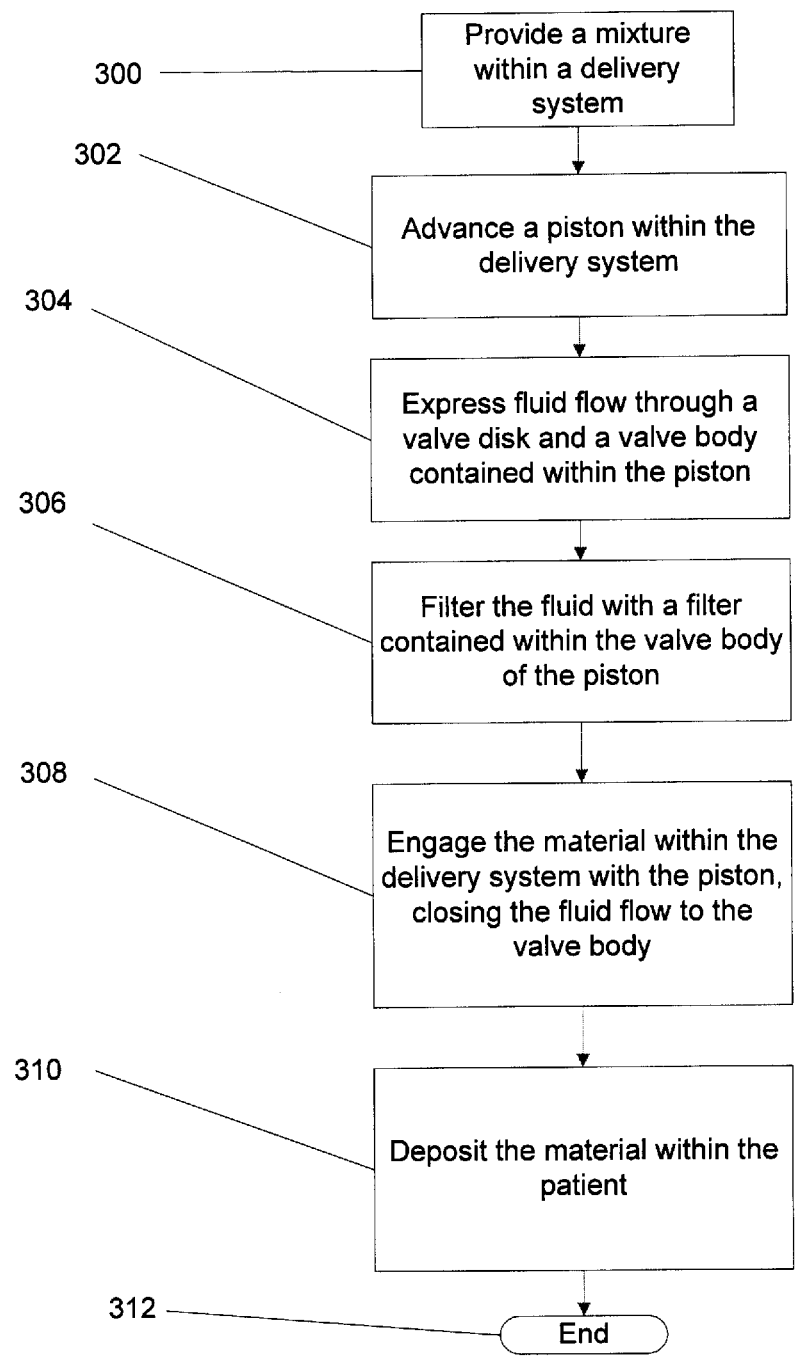
FIG. 3 is a flow chart illustrating a method of using the material delivery system.

Referring to FIG. 3, an exemplary, non-limiting embodiment of a method of treating a patient is shown and commences at block 300. At block 300, a material is provided in the material delivery device. For example, the material is a two-part bone cement mixture of methyl methacrylate monomer and polymethyl methacrylate contained within a syringe. As stated earlier, the two-part bone cement mixture typically releases gaseous vapors which are noxious and toxic.

At block 302, the piston is advanced through the syringe. Advancing the piston can include depressing the stem of the syringe. As the piston is advanced through the syringe, the valve disk contained within the piston is in an open position. The open position of the valve disk allows fluid flow into the valve body. In an embodiment, fluid flow includes the flow of gaseous vapors from the bone cement mixture. In an embodiment, the valve disk is opened to fluid flow by engaging the stem attached to the valve disk. Further, at block 304, fluid flow is expressed through the valve body. Typically, by advancing the piston through the syringe, the fluid flow is expressed. Next, at block 306, the fluid flow that is expressed through the valve body is filtered by the filter contained within the valve body.

Moving to block 308, the piston engages the material within the piston. As the piston engages the material, the valve disk is moved to a closed position wherein the valve disk is closed to fluid flow. In particular, the gaseous vapors are prevented from entering the valve disk and the valve body when the valve disk is in the closed position. Thereafter, at block 310 the material is further advanced through the syringe and deposited in a patient. In a particular embodiment, the material is deposited within a bone within a patient. The method can end at state 312.

CONCLUSION

With the configuration of the structure described above, the material delivery device and the piston include therein provides a device that allows for the nontoxic preparation of noxious and unsafe materials. Further, the piston is a self-contained filtration system that does not necessitate the use of additional vacuums or filtration apparatus attached to the material delivery device. As such, mixing materials such as bone cement using the pistons and material delivery device described herein is safe and user friendly.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A piston configured to be received within a syringe comprising:

a valve body defining a proximal end and a distal end, the proximal end comprising a filter hub and a filter base having a filter disposed therein configured to trap noxious vapors such that the vapors are contained within the filter and the valve body of the piston to prevent release into the environment;

a valve disk disposed within the distal end of the valve body, wherein as the piston is advanced through the syringe, the valve disk is configured to provide fluid flow through the valve body; and a stem including an outer shaft that is fixed to the filter hub and an inner shaft that is fixed to the valve disk such that the outer shaft is spaced apart from the valve disk and the filter, wherein as the piston is advanced through the syringe, the valve disk is configured to move between a first position and a second position, wherein in the first position the valve disk is open to fluid flow and in the second position the valve disk is closed to fluid flow so as to contain the noxious vapors within a sealed valve body of the piston and prevent the noxious vapors from being dispelled through a needle hilt of the syringe.

2. The piston of claim 1, wherein the valve disk is configured to provide fluid communication through the valve body in the first position and the valve disk is configured to prevent fluid communication through the valve body in the second position.

3. The piston of claim 1, wherein the valve body comprises a valve seat formed within the distal end of the valve body, and wherein the valve disk engages the valve seat in the second position.

4. The piston of claim 1, wherein the valve disk moves from the first position to the second position when the valve disk engages a material disposed within the syringe.

5. The piston of claim 1, wherein the valve disk is porous.

6. The piston of claim 5, wherein the valve disk is configured to prevent fluid flow through the valve body when the valve disk engages a material disposed within the syringe.

7. The piston of claim 1, further comprising the syringe, wherein the outer shaft is configured to move the valve body relative to the syringe.

8. The piston of claim 1, wherein the inner shaft is configured to move the valve disk relative to the valve body.

9. The piston of claim 1, wherein the inner shaft is non-cannulated.

10. The piston of claim 1, wherein the inner shaft extends through the filter.

11. The piston of claim 1, wherein a proximal surface of the filter engages a distal surface of the filter base, and a side surface of the filter engages a side surface of the filter base.

12. The piston of claim 1, wherein an outer surface of the filter base comprises a thread form that engages a thread form on an inner surface of the valve body to removably couple the filter base to the valve body.

13. The piston of claim 1, wherein the inner shaft is movable within the outer shaft.

14. The piston of claim 1, further comprising the syringe, wherein:
an outer surface of the valve disk is spaced apart from an inner wall of the syringe; and
outer surfaces of the valve body and the filter base engage the inner wall.

15. The piston of claim 1, wherein the stem defines a longitudinal axis, the filter being positioned such that the filter does not intersect the longitudinal axis.

16. The piston of claim 1, wherein an inner surface of the outer shaft engages an outer surface of the inner shaft and an outer surface of the outer shaft engages an inner surface of the filter hub.

17. A syringe comprising:
a chamber defined by an inner wall; and
a piston configured to engage the inner wall of the chamber, the piston including:
a valve body defining a proximal end and a distal end, the proximal end comprising a filter hub and a filter base having a filter disposed therein configured to trap noxious vapors such that the vapors are contained within the filter and the valve body of the piston to prevent release into the environment;
a valve disk disposed within the distal end of the valve body, wherein as the piston is advanced through the valve body, the valve disk is configured to provide fluid flow through the valve body; and
a stem including an outer shaft that is fixed to the filter hub and an inner shaft that is fixed to the valve disk such that the outer shaft is spaced apart from the valve disk and the filter, wherein as the piston is advanced through the syringe, the valve disk is configured to move between a first position and a second position, wherein in the first position the valve disk is open to fluid flow and in the second position the valve disk is closed to fluid flow so as to contain the noxious vapors within a sealed valve body of the piston and prevent the noxious vapors from being dispelled through a needle hilt of the syringe.

18. The syringe of claim 17, wherein the piston is configured to form a substantially airtight seal with the inner wall of the chamber.

19. The syringe of claim 17, wherein the valve disk is configured to provide fluid communication through the valve body in the first position and the valve disk is configured to prevent fluid communication through the valve body in the second position.

20. The syringe of claim 17, wherein the valve body comprises a valve seat formed within the distal end of the valve body, and wherein the valve disk engages the valve seat in the second position.

21. The syringe of claim 17, wherein the valve disk moves from the first position to the second position when the valve disk engages a material in the chamber.

22. The syringe of claim 17, wherein the valve disk is configured to prevent fluid flow through the valve body when the valve disk engages a material within the chamber.

23. A delivery system comprising:
a syringe comprising an inner wall defining a chamber; and
a piston that movably engages the inner wall, the piston comprising:
a valve body defining a proximal end and a distal end, the proximal end comprising a filter hub and a filter base having a filter disposed therein configured to trap noxious vapors such that the vapors are contained within the filter and the valve body of the piston to prevent release into the environment;
a valve disk disposed within the distal end of the valve body such that the valve disk is spaced apart from the inner wall; and
a stem including an outer shaft that is fixed to the filter hub to move the valve body relative to the syringe and a non-cannulated inner shaft that extends through the filter and is fixed to the valve disk to move the valve disk relative to the valve body, the inner shaft being movable within the outer shaft,
wherein the outer shaft is spaced apart from the valve disk and the filter.

24. The system of claim 23, wherein the stem defines a longitudinal axis, the filter being positioned such that the filter does not intersect the longitudinal axis.

* * * * *

UNITED STATES PATENT AND TRADEMARK OFFICE
CERTIFICATE OF CORRECTION

PATENT NO.         : 8,840,592 B2                              Page 1 of 1
APPLICATION NO.    : 12/046856
DATED              : September 23, 2014
INVENTOR(S)        : Booth, III et al.

It is certified that error appears in the above-identified patent and that said Letters Patent is hereby corrected as shown below:

On the Title Page, item (75), under "Inventors", in Column 1, Line 1, delete "WI" and insert -- MI --, therefor.

On the Title Page, item (75), under "Inventors", in Column 1, Line 3, delete "Vancover (CA);" and insert -- Vancouver (CA); --, therefor.

In the Specification

In Column 1, Line 23, delete "metacrylate" and insert -- methacrylate --, therefor.

In Column 2, Line 61, delete "Valve disk 138" and insert -- Valve disk 140 --, therefor.

In Column 2, Line 62, delete "valve disk 138" and insert -- valve disk 140 --, therefor.

In Column 5, Line 12, delete "metacrylate" and insert -- methacrylate --, therefor.

In Column 5, Line 35, delete "porous disk 240" and insert -- porous disk 238 --, therefor.

Signed and Sealed this
Ninth Day of December, 2014

Michelle K. Lee
*Deputy Director of the United States Patent and Trademark Office*